US006890917B2

(12) United States Patent
Snader et al.

(10) Patent No.: US 6,890,917 B2
(45) Date of Patent: May 10, 2005

(54) GELDANAMYCIN DERIVATIVE AND METHOD OF TREATING CANCER USING SAME

(75) Inventors: Kenneth M. Snader, Germantown, MD (US); B. Rao Vishnuvajjala, Rockville, MD (US); Melinda G. Hollingshead, Middletown, MD (US); Edward A. Sausville, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/432,581

(22) PCT Filed: Mar. 28, 2002

(86) PCT No.: PCT/US02/10097

§ 371 (c)(1),
(2), (4) Date: Sep. 16, 2003

(87) PCT Pub. No.: WO02/079167

PCT Pub. Date: Oct. 10, 2002

(65) Prior Publication Data

US 2004/0053909 A1 Mar. 18, 2004

Related U.S. Application Data

(60) Provisional application No. 60/280,078, filed on Mar. 30, 2001.

(51) Int. Cl.[7] .................... C07D 225/06; A61K 31/395
(52) U.S. Cl. ........................................ 514/183; 540/461
(58) Field of Search ........................... 514/183; 540/461

(56) References Cited

U.S. PATENT DOCUMENTS

| 4,261,989 A | * | 4/1981 | Sasaki et al. ............... 514/183 |
| 5,658,756 A | | 8/1997 | Rodan et al. |
| 5,866,397 A | | 2/1999 | Rodan et al. |
| 5,932,566 A | | 8/1999 | Schnur et al. |
| 5,948,814 A | | 9/1999 | Hwang et al. |
| 5,952,175 A | | 9/1999 | Yue et al. |
| 5,958,892 A | | 9/1999 | Mukhopadhyay et al. |
| 5,968,921 A | | 10/1999 | Gold |
| 6,015,659 A | | 1/2000 | Welch et al. |

FOREIGN PATENT DOCUMENTS

| JP | 55111419 | | 8/1980 |
| JP | 55111469 | | 8/1980 |
| JP | 55111470 | | 8/1980 |
| WO | WO 95/01342 | * | 1/1995 |

OTHER PUBLICATIONS

Sasaki et al., "Growth Inhibition of Virus Transformed Cells In Vitro and Antitumor Activity In Vivo of Geldanamycin and Its Derivatives," *Journal of Antibiotics*, 1979, pp. 849–851, 32(8).
An et al., "Depletion of p185$^{erbB2}$, Raf–1 and mutant p53 proteins by geldanamycin derivatives correlates with antiproliferative activity," *Cancer Chemother. Pharm.* (1997), 60–64, 40.
Kelland et al., "DT–Diaphorase Expression and Tumor Cell Sensitivity to 17–Allylamino, 17–demethoxygeldanamycin, an Inhibitor of Heat Shock Protein 90," *Nat. Cancer Inst.* (1999), 1940–1949, 91.
Kuduk et al., "Synthesis and Evaluation of Geldanamycin–Estradiol Hybrids," *J. Biorg. Med. Chem. Lett.* (1999), 1233–1238, 9.
Kuduk et al., "Synthesis and Evaluation of Geldanamycin–Testosterone Hybrids," *J. Biorg. Chem. Lett.* (2000), 1303–1306, 10.
Mandler et al., "Synthesis and Evaluation of Antiproliferative Activity of a Geldanamycin–Herceptin™ Immunoconjugate," *J. Biorg. Chem. Lett.* (2000), 1025–1028, 10.
Neckers et al., "Geldanamycin as a potential anti–cancer agent: Its molecular target and biochemical activity," *Investigational New Drugs* (1999), 361–373, 17.
Schnur et al., "Inhibition of the Oncogene Product p185$^{erbB-2}$ in Vitro and in Vivo by Geldanamycin and Dihydrogeldanamycin Derivatives," *J. Med. Chem.* (1995), 3806–3812, 38.
Schnur et al., "erbB–2 Oncogene Inhibition by Geldanamycin Derivatives: Synthesis, Mechanism of Action, and Structure—Activity Relationships," *J. Med. Chem.* (1995), 3813–3820, 38.
Webb et al., "The Geldanamycins Are Potent Inhibitors of the Hepatocyte Growth Factor/Scatter Factor–Met–Urokinase Plasminogen Activator–Plasmin Proteolytic Network," *Cancer Res.* (2000), 342–349, 60.

* cited by examiner

*Primary Examiner*—Bruck Kifle
(74) *Attorney, Agent, or Firm*—Leydig, Voit & Mayer, Ltd.

(57) ABSTRACT

A geldanamycin derivative exhibiting significant preliminary in vivo activity, particularly significant oral in vivo activity, and a method of treating or preventing cancer in a host comprising administering a geldanamycin derivative to a host in an amount sufficient to treat or prevent cancer.

30 Claims, No Drawings

GELDANAMYCIN DERIVATIVE AND METHOD OF TREATING CANCER USING SAME

CROSS REFERENCE TO RELATED APPLICATIONS

This patent application claims priority to U S. provisional patent application 60/280,078 filed on Mar. 30, 2001.

FIELD OF THE INVENTION

This invention relates to geldanamycin, and more particularly to novel geldanamycin derivatives, pharmaceutical compositions thereof, and to a method of using such derivatives for the prophylaxis and treatment of cancer.

BACKGROUND OF THE INVENTION

The ErbB2 gene product, which is a member of the ErbB family of receptor tyrosine kinases, is believed to play an important role in the malignancy of tumor cells. Studies have shown that the over-expression of ErbB2 causes cell transformation and tumorgenesis, and in vitro experiments have shown that ErbB2 is required for induction of carcinoma cell invasion by other members of the ErbB family. The benzoquinone ansamycin, geldanamycin, has anti-tumor activity in vivo, and has been shown to cause the rapid depletion of ErbB2 protein levels. Geldanamycin is a specific inhibitor of certain chaperone proteins including the heat shock protein-90 (Hsp90) as well as the glucose-regulated protein-94 (Grp94), which is localized to the endoplasmic reticulum. It is believed that geldanamycin acts on the ErbB2 protein through its inhibition of the Hsp90 chaperone protein, which is thought to be necessary for proper function of the ErbB2 protein. Hsp90 also has been shown to be linked to tumor cell proliferation (see L. Whitesell et al., *Inhibition of Heat Shock Protein HSP-90-pp60v-src Heteroprotein Complex Formation by Benzoquinone Ansamycins: Essential Role for Stress Proteins in Oncogenic Transformation,* 91 Proc. Nat'l Acad. Sci. USA 8324–8328 (1994); T. W. Schulte et al., *Antibiotic Radicicol Binds to the N-terminal Domain of Hsp90 and Shares Important Biologic Activities with Geldanamycin,* 3 Cell Stress and Chaperone Proteins 100–108 (1998); J. L. Johnson et al., *Binding of p23 and Hsp90 During Assembly with the Progesterone Receptor,* 9 Mol. Endocrinol. 670–678 (1995); W. Sullivan et al., *Nucleotides and two functional states of Hsp90,* 272 J. Biol. Chem. 8007–8012 (1997)).

Analogues of geldanamycin have been synthesized in attempts to increase the bioavailability and reduce the toxicity associated with the natural product. Among the more successful analogues is 17-allylaminogeldanamycin (17-AAG), which is currently in phase I clinical trials at the National Cancer Institute. Other similar geldanamycin derivatives substituted at the 17$^{th}$ position exist as possible cancer treatments, such as those described in R. C. Schnur et al., *Inhibition of the Oncogene Product p185$^{erB-2}$ in Vitro and in Vivo by Gedanamycin and Dihydrogeldanamycin Derivatives,* 38 J. Med. Chem. 3806–3812 (1995). While many of these compounds show relatively significant activity in vitro, few exhibit sufficient in vivo activity in preliminary testing. Thus, these compounds represent poor candidates as a potential means of therapeutic treatment. In addition, no known geldanamycin compound or derivative thereof has shown in vivo activity when administered orally.

Thus, a need remains for other effective anticancer compounds and methods of using such compounds. The present invention seeks to fulfill such a need. The particular advantages of the invention, as well as additional inventive features, will be apparent from the description of the invention provided herein.

BRIEF SUMMARY OF THE INVENTION

The invention provides a compound of the formula (I),

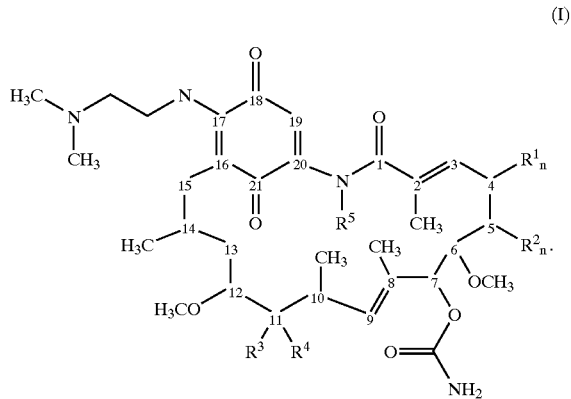

(I)

wherein n=0 or 1 and wherein, when n=1, each of $R^1$ and $R^2$ is hydrogen, and, when n=0, a double-bond exists between $C_4$ and $C_5$;

$R^3$ is hydrogen or hydroxyl;

$R^4$ is hydrogen or hydroxyl; wherein, when $R^3$ is hydrogen, $R^4$ is hydroxyl, and when $R^3$ is hydroxyl, $R^4$ is hydrogen; and $R^5$ is hydrogen or a group of the formula (II)

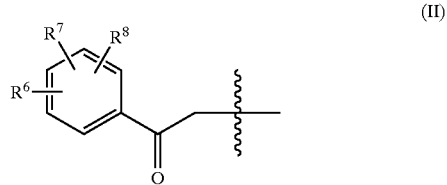

(II)

wherein each of $R^6$, $R^7$, and $R^8$ is independently selected from the group consisting of hydrogen, halo, azido, nitro, a $C_1$–$C_8$ alkyl, a $C_1$–$C_8$ alkoxy, aryl, cyano, and $NR^{10}R^{11}$, wherein each of $R^{10}$ and $R^{11}$ is independently selected from the group consisting of hydrogen and a $C_1$–$C_3$ alkyl; and salts thereof.

The present invention also provides a pharmaceutical composition comprising a compound of the invention and a pharmaceutically acceptable carrier.

A method of treating or preventing cancer in a host is also provided. The method comprises administering to a host the above-described compound in an amount sufficient to treat or prevent cancer in the host, whereupon the cancer of the host is treated or prevented.

DETAILED DESCRIPTION OF THE INVENTION

The invention provides a compound of formula (I),

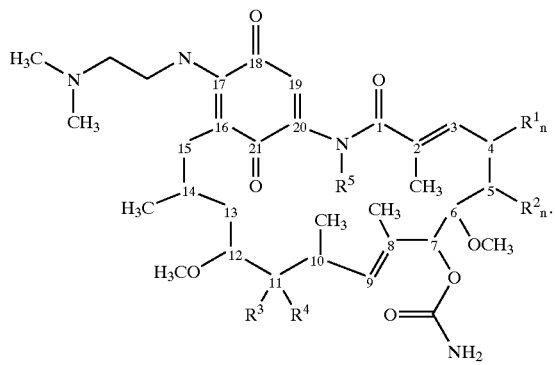

(I)

wherein n=0 or 1. When n=1, each of $R^1$ and $R^2$ is hydrogen and, when n=0, a double-bond exists between $C_4$ and $C_5$. $R^3$ and $R^4$ are each independently hydrogen or hydroxyl, wherein, when $R^3$ is hydrogen, $R^4$ is hydroxyl, and when $R^3$ is hydroxyl, $R^4$ is hydrogen. $R^5$ is hydrogen or a group of the formula (II)

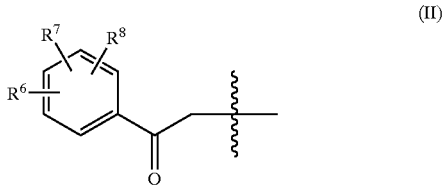

(II)

wherein each of $R^6$, $R^7$, and $R^8$ is independently selected from the group consisting of hydrogen, halo, azido, nitro, a $C_1$–$C_8$ alkyl, a $C_1$–$C_8$ alkoxy, aryl, cyano, and $NR^{10}R^{11}$, wherein each of $R^{10}$ and $R^{11}$ is independently selected from the group consisting of hydrogen and a $C_1$–$C_3$ alkyl. The invention also provides salts of the compound of formula (I). Positions indicated by the numbers 1–21 on the benzoquinone ansamycin ring in formulas (I) and (III) represent carbon atoms.

In a preferred embodiment of the present invention, n=0 and a double bond exists between $C_4$ and $C_5$. Hydrogen is particularly preferred for $R^5$. Thus, a particularly preferred compound of the present invention is a compound represented by formula (III) (17-dimethylaminoethylamino-17-demethoxygeldanamycin).

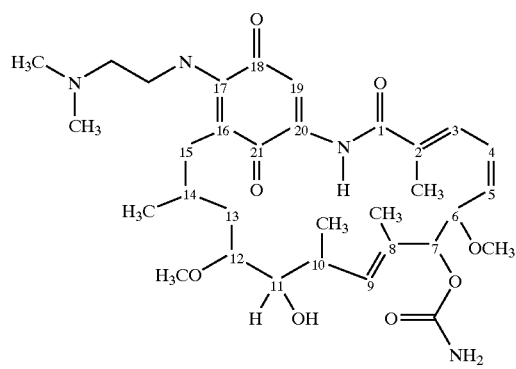

(III)

Compounds of the present invention can be in the form of a salt, which is preferably a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, such as, for example, p-toluenesulphonic acid.

Preferably, the compounds of the present invention have improved water-solubility as compared to Geldanamycin and/or have the ability to form salts (e.g., acid salts) having improved water-solubility as compared to Geldanamycin, while retaining in vitro or in vivo anticancer or antitumor activity. For example, preferred compounds of the present invention have water-solubilities of at least about 0.5 mg/ml or at least about 1 mg/ml (e.g., at least about 1.5 mg/ml), preferably at least about 2 mg/ml (e.g., at least about 2.5 mg/ml). Most preferably, the compounds of the present invention have water-solubilities of at least about 3 mg/ml (e.g., at least about 3.5 mg/ml) or even at least about 4 mg/ml (e.g., at least about 4.5 mg/ml) or even greater water-solubilities (e.g., at least about 5 mg/ml). Water-solubilities can be determined using standard techniques known in the art. While the compounds of the present invention, preferably, have improved water-solubility, techniques known in the art can be used in conjunction with the present invention to further improve the water-solubility of these compounds. For example, the pH of a formulation comprising the compound can be adjusted to optimize the water-solubility of the compound. Also, various additives can be incorporated into a formulation comprising a compound of the present invention. Useful additives include cosolvents (e.g., polyethylene glycol), surface active agents, complexing agents, emulsifying agents, amphiphilic compounds, liposomes, and micro- and nanoparticles, which may improve the solubility of a compound of the present invention.

The compounds of the present invention have been shown to have significant in vivo activity as compared to compounds of similar structure. In vivo activity can be measured by any suitable method known in the art. Suitable methods include, for example, a hollow fiber assay (HFA) and/or xenograft testing. A preferred method of determining in vivo activity used in conjunction with the present invention is a hollow fiber assay, as described in M. G. Hollingshead et al., *In Vivo Cultivation of Tumor Cells in Hollow Fibers*, (57)2 Life Sci. 131–141 (1995). Typically, a hollow fiber assay is used as a preliminary screen to identify compounds having moderate to prominent anti-cancer activity. Generally, compounds which exhibit significant positive results are considered to have moderate to prominent anti-cancer activity. HFA can be used in conjunction with other testing methods, such as xenograft testing, to provide more evidence as to the in vivo anti-cancer activity of compounds and, thus, their suitability for treatment of a particular disease.

It has also been found, unexpectedly, that the compounds of the present invention produce significant oral in vivo activity when administered to a host. By significant oral in vivo activity, it is meant that the compound can be administered orally to a host to produce an HFA score so as to warrant further testing. It should be noted that no other class of geldanamycin compounds or derivatives thereof has shown such significant oral in vivo activity. Therefore, compounds of the present invention would be preferred over other treatment options due to the less invasive means by which the compound can be administered effectively.

The present invention also provides a pharmaceutical composition comprising the geldanamycin compounds of formula (I) described herein. The pharmaceutical composition can further comprise more than one active ingredient. For example, the pharmaceutical composition can comprise more than one compound of the present invention, it can comprise a compound of the present invention in combination with another pharmaceutically active agent or drug, and the like.

The pharmaceutical composition also comprises a suitable carrier. Preferably, the carrier is a pharmaceutically acceptable carrier. With respect to pharmaceutical compositions, the carrier can be any of those conventionally used to make a pharmaceutical composition. The choice of pharmaceutically acceptable carrier is limited only by chemico-physical considerations, such as solubility and lack of reactivity with the active compound(s), and by the route of administration. It will be appreciated by one of skill in the art that, in addition to the following described pharmaceutical composition, the compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well known to those who are skilled in the art and are readily available. It is preferred that the pharmaceutically acceptable carrier be one which is chemically inert to the active compound(s) and one which has no detrimental side effects or toxicity under the conditions of use.

The choice of carrier will be determined in part by the particular compound, as well as by the particular method used to administer the composition. Accordingly, there is a variety of suitable formulations of the pharmaceutical composition of the present invention. The following formulations for oral, aerosol, parenteral, subcutaneous, intravenous, intramuscular, interperitoneal, rectal, and vaginal administration are exemplary and are in no way limiting.

Injectable formulations are among those formulations that are preferred in accordance with the present inventive methods. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238–250 (1982), and *ASHP Handbook on Injectable Drugs*, Toissel, 4th ed., pages 622–630 (1986)). It is preferred that such injectable compositions be administered intravenously or, in the context of the treatment of cancer, intratumorally (within the tumor) or peritumorally (near the outside of the tumor).

Topical formulations are well-known to those of skill in the art. Such formulations are particularly suitable in the context of the present invention for application to the skin.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The present inventive compound, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The present inventive compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5% to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the present inventive compounds, or compositions containing those compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

As discussed previously, geldanamycin derivatives, such as those described herein, inhibit certain chaperone proteins including the heart shock protein-90 (Hsp90) as well as the glucose-regulated protein-94 (Grp94). Hsp90 has been shown to be necessary for proper ErbB2 function. In addition, Hsp90 has been shown to be linked to tumor cell proliferation and ErbB2 is believed to play an important role in the malignancy of tumor cells. In this regard, the present invention further provides a method of treating or preventing cancer in a host. The method comprises administering a compound of the present invention to a host in an amount sufficient to treat or prevent cancer in the host, whereupon the cancer of the host is treated or prevented.

The method of treating cancer using the compound of the present invention can be improved by administering one or more other anticancer compounds along with one or more other compounds of the present invention. These other anticancer compounds include, but are not limited to, the known anticancer compounds approved in the United States and those that will become approved in the future. See, for example, Table 1 and Table 2 of Boyd, *Current Therapy in Oncology*, Section I. Introduction to Cancer Therapy (J. E. Niederhuber, ed.), Chapter 2, by B.C. Decker, Inc., Philadelphia, 1993, pp. 11–22. More particularly, anticancer compounds that are preferably used with the geldanamycin derivatives described herein in accordance with the invention include doxorubicin, bleomycin, vincristine, vinblastine, VP-16, VW-26, cisplatin, carboplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

A compound of the present invention, desirably, is administered to a cell that expresses ErbB2 in the absence of the compound of the present invention, or to a host including such cells, in an amount sufficient to reduce or eliminate the expression of ErbB2 protein. The amount of geldanamycin derivative of the present invention that is administered is an amount sufficient to reduce the expression of ErbB2 by at least about 20%, to completely, as compared to expression of ErbB2 in the absence of the geldanamycin derivatives of the present invention. It will be appreciated by those skilled in the art that reduction in the expression of ErbB2 by at least about 30%, by at least about 40%, by at least about 50%, by at least about 60%, by at least about 70%, by at least about 80%, or by at least about 90% as compared to expression of ErbB2 in the absence of the geldanamycin derivative of the present invention is also beneficial to the host.

Any suitable method to measure expression levels of ErbB2 can be used in conjunction with the present invention. Suitable methods include, for example, differential display, serial analysis of gene expression (SAGE), quantitative reverse transcription-polymerase chain reaction (QRT-PCR), subtraction cloning, macroarrays, and microarrays (e.g., DNA chips). Expression levels of ErbB2 can be measured before administration of the compound, so as to determine proper dosage regimens, as well as during and after administration of the compound so as to determine the compound's bioavailability and efficacy in vivo.

One skilled in the art will appreciate that suitable methods of administering the geldanamycin derivatives of the present invention, and compositions comprising the geldanamycin derivatives of the present invention to an animal, such as a mammal, in particular a human, are available. Although more than one route can be used to administer a particular compound, a particular route can provide a more immediate and more effective reaction than another route. Accordingly, the herein-described methods are exemplary and are in no way limiting.

The dose administered to an animal, such as a mammal, in particular a human, should be sufficient to prevent cancer, delay its onset, or slow (or stop) its progression. One skilled in the art will recognize that dosage will depend upon a variety of factors including the strength of the particular compound employed, as well as the age, species, condition, and body weight of the animal. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of about 0.1 to about 100 mg of one or more of the compounds described above per kg body weight.

EXAMPLES

The following examples further illustrate the present invention but, of course, should not be construed as in any way limiting its scope. Two compounds of the present invention (i.e., Compounds A and B) and one comparative compound (i.e., Compound C) were prepared as described below. Each of these compounds was subsequently used in a hollow fiber assay to determine if the compound produced sufficient in vivo activity so as to warrant further testing.

Compound A

Preparation of 17-Dimethylaminoethylamino-17-demethoxygeldanamycin

A mixture of geldanamycin (1.5 g, 2.68 mmol) (NCI, Lot No. 3059-25-1) and N,N-dimethylethylenediamine (1.5 mL, 13.7 mmol) (Aldrich, Lot No. 04216AL) in dry methylene chloride (30 mL) (Burdick & Jackson, Lot No. BH516) was stirred at room temperature for 1 hour and subsequently poured into ice water (50 mL). After the organic layer and the aqueous layer became visually separated, the aqueous layer was extracted with methylene chloride (2×10 mL). The combined methylene chloride solution was washed with water (2×10 mL), dried with $MgSO_4$ (J.T. Baker, Lot No. E01098) and evaporated in an aspirator. The remaining residue was purified by silica gel chromatography (30 g) (EM Science, Lot No. 325TA509634) eluting with 10% methanol (Chempure, Lot No. M178KMDH) in methylene chloride. The fractions containing product were combined and concentrated in an aspirator. The residue was then dissolved in hot methylene chloride (3 mL), cooled to room temperature and diluted with hexane (60 mL) (Chempure, Lot No. M148KMRC). This mixture was then stirred at room temperature for 30 minutes. A purple powder formed and was collected by filtration, washed with hexane (2×10 mL) and dried at 55° C./0.1 mmHg for 6 hours to give pure target compound. Approximately 1.59 g of 17-Dimethylaminoethylamino-17-demethoxygeldanamycin (96%) was isolated and used in Example 1.

Compound B

Preparation of (17-Demethoxy-17-[[2-(dimethylamino)ethyl]amino]geldanamycin hydrochloride A mixture of geldanamycin (15 g, 26.75 mmol) (SAIC-Frederick, Lot No. 3155-28-1) and N,N-dimethylethylenediamine (15 mL, 37.83 mmol) (Aldrich, Lot No. HN04216AL) in dry methylene chloride (300 mL) (Mallinckrodt, Lot No. 4881KVJP) was stirred at room temperature for 1 hour and subsequently poured into ice water (500 mL). After the organic layer and aqueous layer became visually separated, the aqueous layer was extracted with methylene chloride (2×100 mL). The combined methylene chloride solution was washed with water (2×100 mL), dried with $MgSO_4$ (Spectrum, Lot No. HJ302), and evaporated in a diaphragm pump. The remaining residue (16.5 g, 26.75 mmol) was dissolved in methylene chloride (130 mL). Dissolved hydrogen chloride (1.1 eq, 29.43 mmol) (Matheson, Lot No. T410242) in dioxane (Aldrich, Lot No. 16619CQ) was added to the solution resulting in immediate precipitation. After stirring for 30 minutes, the solids were collected, rinsed with methylene chloride (50 mL), and air-dried for 18 hours to give the crude hydrochloride salt (17.2 g). A solution of the crude product (17.2 g) in aqueous alcohol (50% v/v, 200 mL) (Aaper Alcohol, Lot. No. 97A28UARAT) was heated to reflux, filtered, and allowed to cool for 30 minutes. After cooling on ice for an additional 30 minutes, the solids were collected, washed with cold anhydrous alcohol (50 mL), and air-dried for 1 hour. The product was dried further at 70° C./0.1 mmHg for 17 hours to give pure target compound. Approximately 13.4 g of 17-Demethoxy-17-[[2(dimethylamino)ethyl]amino] geldanamycin hydrochloride (82%) was isolated as a violet crystalline solid and used in Examples 1 and 2.

Compound C

Preparation of 17-Dimethylaminopropylamino-17-demethoxygeldanamycin

A mixture of geldanamycin (1.5 g, 2.68 mmol) (NCI, Lot No. 3059-25-1) and 3-dimethylaminopropylamine (1.5 mL, 11.9 mmol) (Aldrich, Lot No. 08103CF) in dry methylene chloride (30 mL) (Burdick & Jackson, Lot No. BH516) was stirred at room temperature for 30 minutes and subsequently poured into ice water (50 mL). After the organic layer and the aqueous layer became visually separated, the aqueous layer was extracted with methylene chloride (2×100 mL). The combined methylene chloride solution was washed with water (2×100 mL), dried with $MgSO_4$ (J.T. Baker, Lot No. E01098) and evaporated in an aspirator. The remaining residue was purified by silica gel chromatography (30 g) eluting with 10% methanol in methylene chloride. The fractions containing product were combined and concentrated in an aspirator. The residue was then dissolved in hot methylene chloride (3 mL), cooled to room temperature and diluted with hexane (60 mL) (Chempure, Lot No. M148KMRC). The resulting mixture was stirred at room temperature for 30 minutes. A purple powder formed and was collected by filtration, washed with hexane (2×10 mL) and dried at 55° C./0.1 mmHg for 5 hours to give pure target compound. Approximately 1.64 g of 17-Dimethylaminopropylamino-17-demethoxygeldanamycin (97%) was isolated and used in Example 1.

The HFA and MTT Assays

Compounds A–C were tested in a hollow fiber assay for in vivo activity. Each compound was tested against a standard panel of 12 human tumor cell lines including NCI-H23, NCI-H522, MDA-MB-231, MDA-MB-435, SW-620, COLO 205, LOX IMVI, UACC-62, OVCAR-3, OVCAR-5, U251 and SF295. The cell lines were cultivated in RPMI-1640 containing 10% FBS and 2 mM glutamine. On the day preceding hollow fiber preparation, the cells were given a supplementation of fresh medium to maintain log phase growth. For fiber preparation, the cells were harvested by standard trypsinization technique and resuspended at the desired cell density. The cell suspensions were flushed into 1 mm polyvinylidene fluoride (PVDF) hollow fibers (MW exclusion of 500,000 Da) and subsequently heat-sealed at 2 cm intervals. The samples generated from these seals were placed into tissue culture medium and incubated at 37° C. in 5% $CO_2$ for 24–48 hours prior to implantation. A total of 3 different tumor cell lines were prepared for each experiment so that each mouse received 3 intraperitoneal implants (1 of each tumor cell line) and 3 subcutaneous implants (1 of each tumor cell line). A total of 4 experiments were conducted on each mouse (3 cell lines/experiment×4 experiments=12 cell lines).

On the day of implantation, samples of each tumor cell line were quantitated for viable cell mass by a stable endpoint MTT assay so that the time 0 cell mass was known. In the MTT assay, the fibers were incubated in 6-well plates (1–6 fibers/well) with 3 mL of pre-warmed (37° C.) complete medium containing MTT (1 mg/mL) (Sigma) for 4 hours at 37° C. in 5% $CO_2$. The MTT solution was aspirated and the fibers were washed with 2 mL of saline containing 2.5% protamine sulfate overnight at 4° C. A second wash was performed with 2 mL of saline containing 2.5% protamine sulfate, and the fibers were maintained at 4° C. for a minimum of 2 hours. The fibers were then removed from the protamine sulfate, individually wiped, placed in a 24-well plate (1 fiber/well), cut in half and dried overnight in a biosafety hood. To extract the formazan, DMSO was added (0.25 mL) to each well and the plates were rotated for 4 hours at room temperature. The extracted samples were transferred to 96-well plates and the OD was determined at 540 nm. From these spectrophotomeric measurements, the cytostatic and cytocidal capacities of the test compound were assessed.

Following implantation of the hollow fibers, mice were treated with one of the compounds, as listed in Tables 1 and 2 starting on day 3 or 4 following fiber implantation and continuing once daily for a total of 4 doses. Each compound was either assessed by intraperitoneal injection (Example 1) or by oral administration (Example 2) at 2 dose levels with 3 mice/dose/experiment. Vehicle controls consisted of 6 mice receiving the compound diluent only. The fibers were collected from the mice on the day following the fourth compound treatment and subjected to the stable endpoint MTT assay. The optical density of each sample was determined spectrophotometrically at 540 nm and the mean of each treatment group was calculated. The percent net cell growth in each treatment group was determined and compared to the percent net cell growth in the vehicle treated controls.

In the context of the following examples, compounds were selected for further testing (e.g., time/dose exposure studies, preliminary pharmacology studies, subcutaneous xenograft efficacy studies) on the basis of several hollow fiber assay criteria, including (1) a reduction in net cell growth of 50% or greater in 10 of the 48 possible test combinations; (2) a reduction in net cell growth of 50% or greater in a minimum of 4 of the 24 distant site combinations (SC score); and/or (3) cell kill of 1 or more cell lines in either implant site (reduction in the viable cell mass below the level present at the start of the experiment).

To simplify evaluation, a point system was adopted which allows rapid viewing of the activity of a given compound. For this, a value of 2 was assigned for each compound dose, which results in a 50% or greater reduction in viable, cell mass. The intraperitoneal (IP) and subcutaneous (SC) samples were scored separately so that criteria (1) and (2) could be evaluated independently.

Example 1

This example demonstrates the in vivo activity of compounds of the present invention as compared to a geldanamycin derivative of similar structure.

A hollow fiber assay was conducted with Compounds A–C, as described above. Compounds A and B were mixed with saline and tween 80 (0.05%) to obtain two dose levels of 75 mg/kg/dose and 50 mg/kg/dose, respectively. Compound C was also mixed with saline and tween 80 (0.05%) to obtain two dose levels of 20 mg/kg/dose and 13.4 mg/kg/dose, respectively. Optimal dosage levels were determined from previous toxicity studies and therefore the dosages used represent the upper range that can be administered to a host without inducing toxic effects. All three compounds were administered once daily for four days via intraperitoneal injection. After four days, the hollow fibers were removed from the mice and subjected to the MTT assay as described above. The percent cell growth inhibition was calculated [(1−(% treated net growth/% control net growth))*100] and an HFA score was assigned to each compound on the basis of this calculation, as indicated in Table 1.

TABLE 1

| Compound | Route of Administration | Dose/Units (mg/kg/dose) | IP Score | SC Score | Total HFA Score |
|---|---|---|---|---|---|
| A | IP | 75 | 20 | 10 | 30 |
|   | IP | 50 |   |   |   |
| B | IP | 75 | 24 | 18 | 42 |
|   | IP | 50 |   |   |   |
| C | IP | 20 | 14 | 2 | 16 |
|   | IP | 13.4 |   |   |   |

As indicated by the results, compounds of the present invention (e.g., Compounds A and B) each produce significantly higher HFA scores and, thus, significantly greater in vivo anti-cancer activity, than a compound not of the present invention (e.g., Compound C).

Example 2

This example demonstrates the oral in vivo activity of a compound of the present invention.

A hollow fiber assay was conducted with Compound B of the present invention, as described above. Compound B was mixed with water to obtain two dosage levels of 75 mg/kg/dose and 50 mg/kg/dose, respectively. The Compound B was then administered orally (PO) once daily for four days. After four days, the hollow fibers were removed from the mice and subjected to the MTT assay as described above. The percent cell growth inhibition was calculated [(1−(% treated net growth/% control net growth))*100] and an HFA score was assigned to each compound on the basis of this calculation, as indicated in Table 2.

TABLE 2

| Compound | Route of Administration | Dose/Units (mg/kg/dose) | IP Score | SC Score | Total HFA Score |
|---|---|---|---|---|---|
| B | PO | 75 | 10 | 10 | 20 |
|   | PO | 50 |   |   |   |

Based on the results indicated above, Compound B of the present invention exhibited significant in vivo anti-cancer activity by oral administration.

All of the references cited herein, including patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly, this invention includes all modifications encompassed within the spirit and scope of the invention as defined by the following claims.

What is claimed is:

1. A compound having the formula:

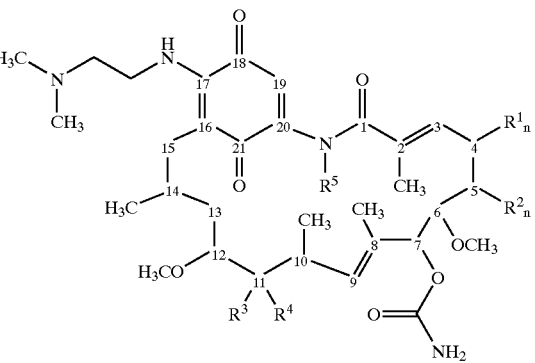

wherein n=0 or 1 and wherein, when n=1, each of $R^1$ and $R^2$ is hydrogen, and, when n=0, a double-bond exists between $C_4$ and $C_5$;

$R^3$ is hydrogen or hydroxyl;

R⁴ is hydrogen or hydroxyl; wherein, when R³ is hydrogen, R⁴ is hydroxyl, and when R³ is hydroxyl, R⁴ is hydrogen; and R⁵ is hydrogen or a group of the formula

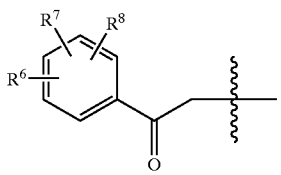

wherein each of $R^6$, $R^7$, and $R^8$ is independently selected from the group consisting of hydrogen, halo, azido, nitro, a $C_1$–$C_8$ alkyl, a $C_1$–$C_8$ alkoxy, aryl, cyano, and $NR^{10}R^{11}$, wherein each of $R^{10}$ and $R^{11}$ is independently selected from the group consisting of hydrogen and a $C_1$–$C_3$ alkyl; or a pharmaceutically acceptable salt thereof.

2. The compound of claim 1, wherein n=0.

3. The compound of claim 2, wherein $R^5$ is hydrogen.

4. A pharmaceutical composition comprising the compound of claim 1 and a pharmaceutically acceptable carrier.

5. A pharmaceutical composition comprising a compound of the formula

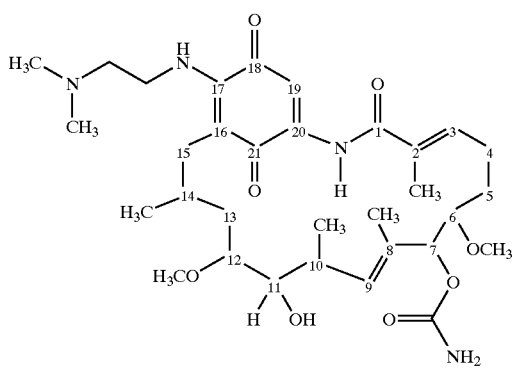

or a pharmaceutically acceptable salt thereof and a pharmaceutically acceptable carrier.

6. A method of treating cancer in a host comprising administering to a host a compound of claim 1 in an amount effective to treat cancer in the host, wherein the cancer is leukemia, non-small cell lung cancer, colon cancer, cancer of the central nervous system, melanoma, ovarian cancer, renal cancer, prostate cancer, or breast cancer.

7. The method of claim 6, wherein the compound is administered orally.

8. The method of claim 6, wherein the host is a mammal.

9. The method of claim 8, wherein the mammal is a human.

10. A method of treating cancer in a host comprising administering to a host a compound in an amount effective to treat cancer in the host, wherein the compound is

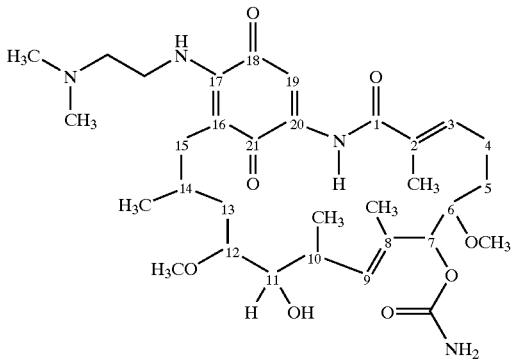

or a pharmaceutically acceptable salt thereof, and wherein the cancer is leukemia, non-small cell lung cancer, colon cancer, cancer of the central nervous system, melanoma, ovarian cancer, renal cancer, prostate cancer, or breast cancer.

11. The method of claim 10, wherein the compound is administered orally.

12. The method of claim 10, wherein the host is a mammal.

13. The method of claim 12, wherein the mammal is a human.

14. The method of claim 6, wherein the compound is administered intravenously.

15. The method of claim 10, wherein the compound is administered intravenously.

16. A compound of the formula:

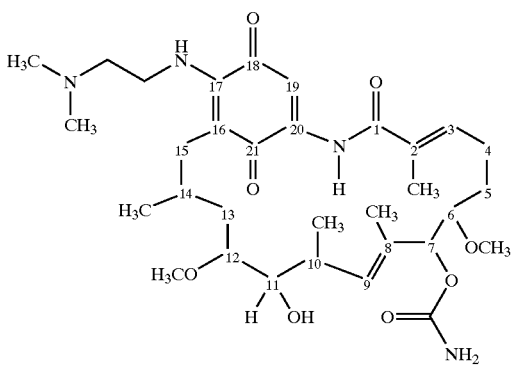

or a pharmaceutically acceptable salt thereof.

17. The method of claim 6, wherein the cancer is breast cancer.

18. The method of claim 10, wherein the cancer is breast cancer.

19. The method of claim 6, wherein the cancer is non-small cell lung cancer.

20. The method of claim 10, wherein the cancer is non-small cell lung cancer.

21. The method of claim 6, wherein the cancer is colon cancer.

22. The method of claim 10, wherein the cancer is colon cancer.

23. The method of claim 6, wherein the cancer is cancer of the central nervous system.

24. The method of claim 10, wherein the cancer is cancer of the central nervous system.

25. The method of claim 6, wherein the cancer is melanoma.

26. The method of claim 10, wherein the cancer is melanoma.

27. The method of claim 6, wherein the cancer is ovarian cancer.

28. The method of claim 10, wherein the cancer is ovarian cancer.

29. The method of claim 6, wherein the cancer is leukemia.

30. The method of claim 10, wherein the cancer is leukemia.

* * * * *

UNITED STATES PATENT AND TRADEMARK OFFICE
CERTIFICATE OF CORRECTION

PATENT NO.    : 6,890,917 B2
DATED         : May 10, 2005
INVENTOR(S)   : Snader et al.

It is certified that error appears in the above-identified patent and that said Letters Patent is hereby corrected as shown below:

Column 13,
Lines 33-49, please delete the compound and substitute the following compound:

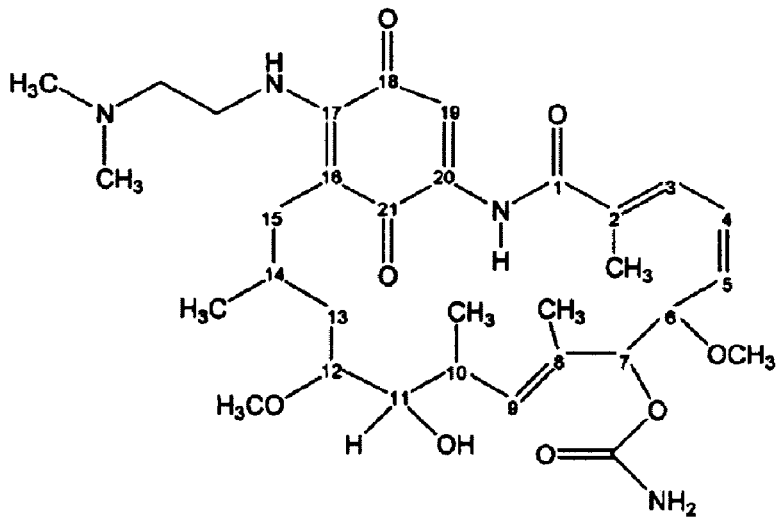

Column 14,
Lines 4-19, please delete the compound and substitute the following compound:

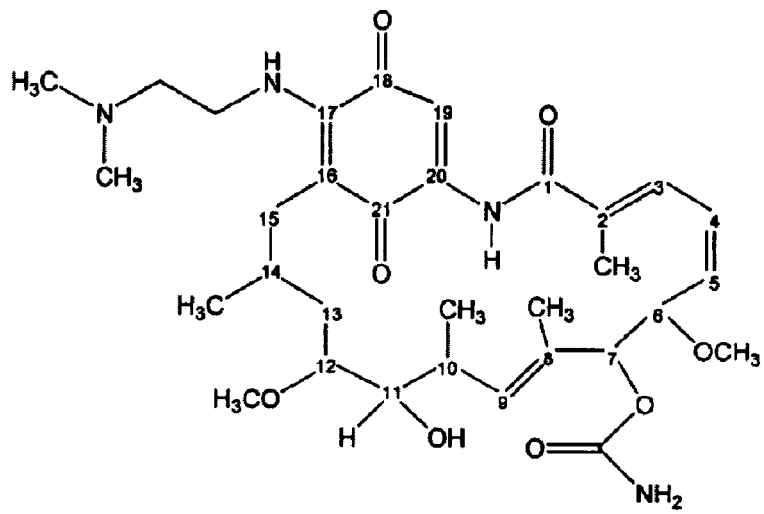

UNITED STATES PATENT AND TRADEMARK OFFICE
CERTIFICATE OF CORRECTION

PATENT NO.    : 6,890,917 B2
DATED         : May 10, 2005
INVENTOR(S)   : Snader et al.

It is certified that error appears in the above-identified patent and that said Letters Patent is hereby corrected as shown below:

Column 14 (cont'd),
Lines 39-54, please delete the compound and substitute the following compound:

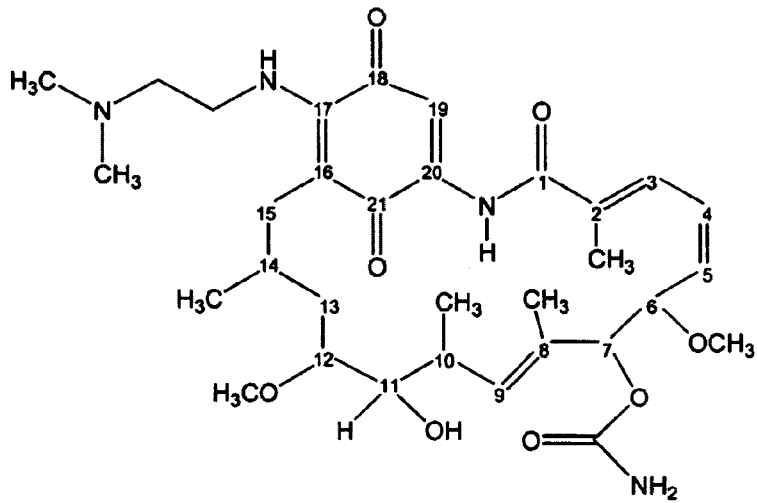

Signed and Sealed this

Fifteenth Day of November, 2005

JON W. DUDAS
*Director of the United States Patent and Trademark Office*